United States Patent [19]
Goldstein et al.

[11] Patent Number: 4,584,075
[45] Date of Patent: Apr. 22, 1986

[54] PROCESS AND APPARATUS FOR ELECTRICALLY DESORBING COMPONENTS SELECTIVELY SORBED ON AN ELECTROLYTICALLY CONDUCTING BARRIER

[75] Inventors: Arthur L. Goldstein; Edgar Haber, both of Weston; Robert J. Mandle, Lexington, all of Mass.

[73] Assignee: Ionics Incorporated, Watertown, Mass.

[21] Appl. No.: 675,057

[22] Filed: Nov. 26, 1984

[51] Int. Cl.$^4$ ............................................. C07K 3/18
[52] U.S. Cl. ........................ 204/182.3; 204/182.4; 204/182.6; 204/301
[58] Field of Search ............... 204/180 P, 263, 296, 204/301

[56] References Cited

U.S. PATENT DOCUMENTS

| | | | |
|---|---|---|---|
| 3,450,630 | 6/1969 | Bloch et al. | 204/180 P |
| 3,839,162 | 10/1974 | Ammer | 204/263 |
| 3,846,270 | 11/1974 | Muto et al. | 204/263 |
| 3,847,788 | 11/1974 | Wallace | 204/301 |
| 4,400,250 | 8/1983 | Fairhurst | 204/301 |
| 4,455,370 | 6/1984 | Bartelsman et al. | 204/403 |
| 4,484,989 | 11/1984 | Mansell | 204/296 |

FOREIGN PATENT DOCUMENTS

| | | | |
|---|---|---|---|
| 1387457 | 6/1964 | France | 204/180 P |
| 0088671 | 8/1978 | Japan | 204/180 P |
| 0128584 | 11/1978 | Japan | 204/180 P |
| 0126679 | 10/1979 | Japan | 204/301 |

Primary Examiner—John F. Niebling
Assistant Examiner—Terryence Chapman
Attorney, Agent, or Firm—Norman E. Saliba

[57] ABSTRACT

Processes and apparatuses are described for recovering components dispersed in an aqueous solution comprising contacting said solution as a first solution with an electrically conducting barrier, diaphragm or membrane which has a high affinity for at least one of said components whereby a substantial fraction of said component is sorbed by said barrier. The barrier is subsequently contacted with a second aqueous solution and a direct electric current is passed through said barrier and second solution in a direction substantially parallel to the smallest dimension of the barrier thereby facilitating desorption of at least one of the sorbed components from the barrier into the second solution which solution is thereafter removed.

9 Claims, 4 Drawing Figures

PROCESS AND APPARATUS FOR ELECTRICALLY DESORBING COMPONENTS SELECTIVELY SORBED ON AN ELECTROLYTICALLY CONDUCTING BARRIER

BACKGROUND OF THE INVENTION

1. Field of the Invention

Affinity chromatography has become a valuable tool for separating biological materials, for example biologically active molecules such as small ligands, proteins, nucleic acids, enzymes, etc. In affinity chromatography, a substrate is immobilized on a granular support during the chromatography. By utilizing a column of said granular immobilized substrate, materials having affinity or binding specificity for the compounds bonded to the stationary phase can be separated from other materials in a mixture.

Typically, complex polysaccharide granules such as agarose beads, etc. are employed in affinity chromatography. The material of the granules may inherently have the desired sorption specifity or a suitable ligand may be bonded, often through so-called spacer-arms, to the granules by a variety of methods. Components in an ambient solution which have a high binding affinity for the materials of the granules or for the ligand will be preferentially bound to the granules. The bound components may be subsequently removed from the granules by contacting the latter with a solution which reduces the binding of the component for the material of the granules or for the ligand. Typically such desorption is accomplished by a substantial change in pH or ionic strength. Alternatively the sorbed component may be desorbed by another ligate which competes for the binding sites. Often chaotropic agents are used which by altering the secondary structure of the sorbed component effect desorption.

Examples of high specific ligands are:
- Lictin absorbents for binding glycoproteins, glycolipids, polysaccharides, and related substances;
- Protein A from Staphylococcus aureus for binding many immunoglobulins;
- Cibacron ® Blue F3G-A for binding albumin, interferons, growth factors, kinases and dehydrogenases;
- Monoclonal antibodies for binding biospecific antigens;
- Biospecific antigens for binding monocloncal antibodies and
- Hydrophobic groups (e.g. aliphatic or aromatic moieties) for binding proteins having hydrophobic regions.

Desorption of tightly bound, high molecular weight ligates is generally a rather slow process and in the presence of substantial changes in pH, ionic strength or high concentrations of chaotropic reagents may result in alterations in biological activity of the ligate or loss of biospecificity of the ligands.

It is an object of the present invention to provide processes and apparatuses which enable the comparatively rapid and economic recovery of bioactive ligates under comparatively gentle desorption conditions, thereby preserving a substantial fraction of the bioactivity.

These and other objects will become apparent from the following description of the invention.

2. Description of the Prior Art (A) P. J. Brown et al (FEBS Letters, Vol. 83, No. 2, Nov. 1977 pp. 256–259) describe the absorption of antigen ligates on columns of granules having antibody ligands. Electrodes were subsequently placed at the top and bottom of the columns and a direct current passed for about one hour to remove the antigen by electrophoresis. The bioactivity of the recovered antigen was not reported.

(B) M. R. A. Morgan et al (J. Immun. Methods 23 (1978) pp. 381–387) describe sorption of immunoglobulin ligates in columns of beads in which the ligands were antisera to the immunoglobulins or Protein A from S aureus. The beads were placed on top of polyacrylamide disc gels. A direct current potential of 50 volts was applied for 4 to 5 hours and the ligates removed by electrophoresis. The bioactivity of the recovered sorbate was not reported.

(C) M. J. Igbal et. al. (FEBS Letters, Vol. 87, No. 2, March 1978, pp. 235–238) describe sorption of a hormone binding globulin by stirring with beads having ligands of androstanediol. The beads were transferred to a column having electrodes at either end. A direct current potential of 110 volts was applied for 5 hours which resulted in removal of the ligate. Substantial denaturation of the recovered ligate was reported.

(D) M. R. A. Morgan et al. (Analyt. Biochem. 105, pp. 1–5, 1980) describe the sorption of albumin in columns of beads having ligands of Cibacron ® Blue F3G-A. The beads were subsequently placed on top of a column of polyacrylamide gel. Direct electric current was passed between electrodes located at the top and bottom of the column. The albumin was eluted electrophoretically. Elution times required to obtain substantial recoveries of albumin were 10 to 20 hours. The degree of denaturation of the albumin was not reported.

DESCRIPTION OF PREFERRED EMBODIMENTS

Figure 1A:
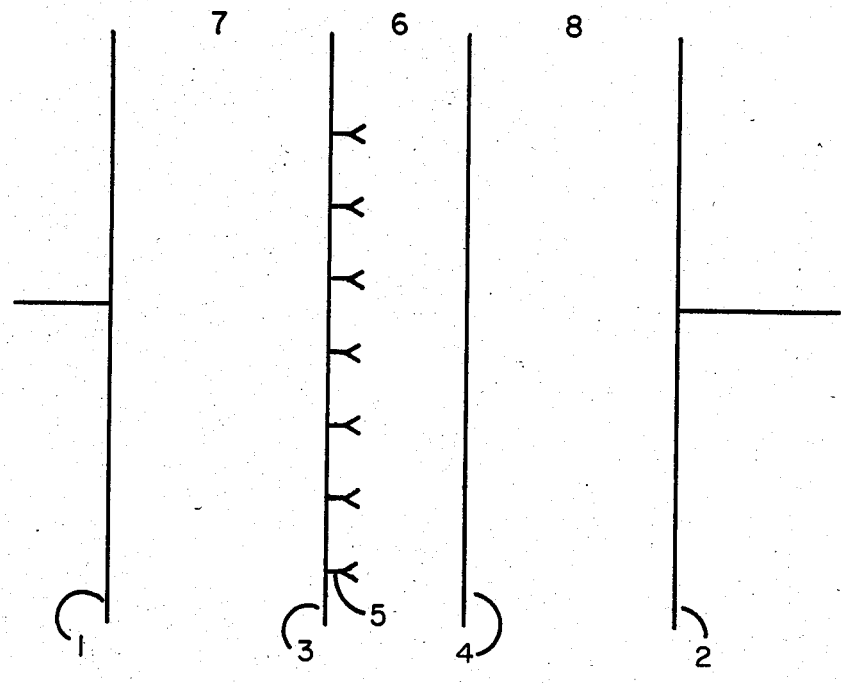
FIG. 1 (a) is a schematic representation of one embodiment of an apparatus having an electrolytically conducting, biospecific absorbing barrier in accordance with the present invention.
FIG. 1(b) is a schematic representation of the apparatus of FIG. 1(a) in the sorbed state and desorption mode.
FIG. 1(c) is a schematic representation of a second embodiment of an apparatus having electrolytically conducting biospecific absorbing barriers in accordance with the present invention, in the sorbed state and desorption mode.

In its broadest aspect, the apparatus of the present invention consists of at least one barrier in the shape of an electrolytically conducting film, membrane or diaphragm having biospecific sorbing properties on at least one major surface and positioned between a pair of electrodes. Either or both of the electrodes may be in contact with the membrane. There may be an array of several electrolytically conducting, biospecific sorbing barriers between the pair of electrodes defining solution compartments between the membranes. Alternatively there may be an array of several electrolytically conducting, biospecific sorbing barriers alternating with electrolytically conducting, substantially non-sorbing barriers.

Referring to FIG. 1 (a) there is indicated a three-compartment electrolytic cell having a pair of electrodes 1 and 2, an electrolytically conducting barrier 3 having biospecific sorbing groups 5 on at least on surface. There is also indicated an optional second electrolytically conducting barrier 4 positioned to protect the sorbing groups 5 and/or ligands sorbed thereon or desorbed therefrom from the products of electrolysis as electrode 2. It will be understood that if the sorbing groups and the ligands sorbed thereon are not sensitive to the electrolysis products, then barrier 4 may be eliminated.

Barrier 3 may comprise an inherently electrolytically conducting material such as an ion exchange resin in the form of sheets or films; preferably having a microporous extended surface for example a macroreticular surface; hydrous material such as a hydrated gel; or a porous material containing water or an aqueous solution in the pores. Examples of suitable hydrous material are agarose gels, zein, collagen and polyacrylamide gels in the form of sheets. Other suitable hydrous gels will be obvious to those skilled in the art. The sheets are preferably reinforced with woven or non-woven fabrics to improve the mechanical strength and handling properties.

Examples of suitable porous materials are films of Cuprophan ® cellulose acetate and nylon or inorganic diaphragms such as ceramic diaphragms, all generally having average pore sizes less than about 10 micrometers which inhibit convective mixing of liquids though the barrier. The barrier material may have inherent biospecific sorbent properties as in the case of zein, collagen and gels containing transitional metal chelates or biospecific ligands may subsequently be added to the accessible surface on one or both principal faces of the barrier. Such ligands may be more or less permanently sorbed on the barrier material as for example, certain antibodies can be sorbed on the available surfaces of zein or collagen barriers by incubating the latter for prolonged periods in a dispersion of the former. It appears that secondary bonds that were previously formed between the substrate protein molecules form between the antibody and the substrate. On the other hand the barrier material may be activiated in various ways know in the art, for example with cyanogen bromide, trichloro-s-triazine, isocyanate, glutaraldehyde and the like as appropriate to the barrier material and the desired ligand. Suitable activating agents are well-known in the art. The ligands may be bound directly to the accessible barrier surface or through leashes, tethers, spacerarms or other stand-offs depending primarily on the size of the ligand or the target ligate. Suitable stand-offs are well known Preferred ligands show a high structural selectivity for the desired ligate and also possess second functional sites at which immobilization to the barrier may be affected without substantially affecting ligate binding. Depending on the target ligate, a wide variety of ligands may be used. The following table illustrates the various classes, but is not intended to limit the scope of this invention.

| Target Ligate | Suitable Ligand |
|---|---|
| 1. Enzymes, apoenzymes | Inhibitor, cofactor, prosthetic group, polymeric substrate |
| 2. Polymeric Inhibitors | Enzymes |
| 3. Nucleic acid, single strand | Nucleic acid complementary strand |
| 4. Antibody | Hapten, antigen |
| 5. Proteins, polysaccharides | Antibody |
| 6. Lectins, receptors | Monosaccharide, polysaccharide |
| 7. Glycoproteins, receptors | Lectin |
| 8. Binding proteins | Small target compounds |
| 9. Small target compounds | Binding protein |
| 10. Trypsin, thrombin, urokinase | Aminobenzamidine |
| 11. Nicotine adenine dinucleotide dependent dehydrogenases | 5' adenosine monophosphate |
| 12. Immunoglobulin G | *S. aureus* Protein A |
| 13. Albumin, coagulation factors, interferon | Cibacron ® Blue F3G-A |
| 14. Serum proteins, interferon | Chelated transition metals |
| 15. Lactalbumin, catalase ferritin, cytochrome C | Octyl or phenyl moieties |

A preferred method of using the above described apparatus is as follows:

The aqueous solution or suspension containing the target molecule(s) is passed or recirculated over the biospecific surface(s) of the barrier(s) 3. Preferably the velocity of the solution or the suspension is sufficient to enhance convective transfer of the target ligate to the biospecific surface. Preferably the distance between the biospecific surface and the adjacent protective barrier 4 (or to the adjacent electrode 2 if the protective barrier 4 is not required) is in the range of from about 0.5 mm to about 5 mm. Mass transfer of the target ligate to the biospecific surface may be enhanced by including between the biospecific surface and the protective membrane 4 (or the electrode 2 if the protective membrane is not required) a convection enhancing structure, for example, a coarse non-woven screen of inert material, e.g. of polypropylene. It is desirable if the combination of solution or suspension velocity, distance between the biospecific surface and the next barrier 4 (or the electrode 2 as the case may be) is such that the average thickness of the unstirred (diffusion) layer against the biospecific surface is not substantially greater than about 0.1 mm. Under such circumstances the rate of sorption of the target ligate will be comparatively rapid.

When the biospecific surface(s) has been substantially saturated and/or the ligate containing solution or suspension has been substantially depleted of target ligate(s), the solution or suspension is withdrawn from further contact with the biospecific surface and the latter rinsed with pure water or other appropriate aqueous solutions to remove traces of the ligate containing solution or suspension and/or to remove non-specifically sorbed components from the biospecific surface. The apparatus is then ready for desorption of one or more of the sorbed ligates with the facilitation of a direct electric current.

Several desorption modes are contemplated. One of these may be described with reference to FIG. 1(b) in which 5 represents a biospecific ligand attached to the barrer 3, 9 represents a ligate complexed with the ligand 5, 6 represents a compartment defined by the barrier 3 and the barrier 4, 7 represents a compartment defined between the barrier 3 and and the electrode 1 (or in the case where several barriers are arranged between a single pair of electrodes, the compartment defined between the barrier 3 and another barrier generally similar in properties to barrier 4), 8 represents a compartment defined by the barrier 4 and the electrode 2 (or in the case where several barriers are arranged between a single pair of electrodes, the compartment defined between the barrier 4 and another barrier generally similar in properties to barrier 3). In the embodiment of this invention represented in FIG. 1(b), compartment 7 is filled with an appropriate acid solution which may be, for example, a dilute solution of a strong acid, a weak acid or of an acidic buffer. Compartment 6 is filled with an appropriate liquid, the choice depending on both the ligand (s) and the ligate(s), generally a buffer solution or pure water. Electrode 1 is made anodic and electrode 2 cathodic causing the transport of hydrogen ions across barrier 3 to the interface between barrier 3 and the liquid in compartment 6. In a preferred method of operation, the electric current is continued for a period sufficient to reduce the pH at the interface to a value at which the ligate-ligand complex dissociates and the ligate begins to diffuse away from the interface into the bulk liquid in compartment 6, but not for a period long enough to substantially alter the pH of the bulk liquid in compartment 6. According to such preferred method, the liquid in compartment 6 is not flowing during the period in which the electric current flows. Again in accordance with said method, after the flow of electric current ceases (or is reduced to a maintenance value), the diffusion of the dissociated ligate(s) into the bulk liquid is allowed to continue for some minutes before the contents of compartment 6 are removed. The duration of such diffusion period depends on the diffusion constant(s) of the ligate(s) (and therefore generally on the molecular weight) and also on the hydrodrynamics of the flow in compartment 6, but is generally sufficiently long to permit a substantial fraction of the ligate to diffuse a distance of at least 0.1 mm. Compartment 6 is then drained rapidly, preferably by imposing a rapid flow of liquid through the compartment, said rapid flow being sufficient (in conjunction with the compartment spacing and any convection enhancing structure) to scour the region near the biospecific surface. In this way the first compartment volume of liquid issuing from compartment 6 will contain a substantial fraction of the dissociated ligate at a comparatively high concentration.

It will be seen that by this method, the dissociating reagent is applied substantially only in the region which contains the ligand-ligate complex and the dissociated ligate(s) (and ligand) is (are) exposed to the dissociating entity for only a short period of time compared with the conventional affinity chromatography methods using granules. It is found therefore that the dissociating conditions are particularly gentle and comparatively little denaturation of the ligate occurs, resulting in higher recoveries (yields) of bioactivity.

It will also be undestood that owing to the exquisite control possible with electrically facilitated desorption it will often be possible to effect the selective desorption of one or more ligates while simultaneously maintaining the sorption of one or more other ligates.

The operation of the apparatus of FIG. 1(b) has been described by reference to effecting an alteration in pH at the biospecific surface. Alternatively, compartment 7 may contain a chaotropic agent such as guanidine hydrochloride in which case gaunidinium cations will be transferred across the barrier to the biospecific surface resulting in dissociation of the ligate(s). Subsequent steps in the operation will be substantially as described above. Dissociation may also be effected by causing a substantial change in the ionic strength at the biospecific surface by passage of electric current. This is particularly effective and efficient when the barrer 3 is ion selective, for example when it comprises an ion exchange resin. If the ligate will be dissociated by an increase in ionic strength and if the barrier 3 is cation selective, then electrode 1 should be anodic and electrode 2 cathodic. It will be obvious to those skilled in the art that if barrier 3 is anion selective then electrode 1 should be cathodic and electrode 2 anodic. On the other hand if the ligate will be dissociated by a decrease in ionic strength (as, for example, when the ligands are hydrophobic groups) and if the barrier 3 is cation selective then electrode 1 should be cathodic and electrode 2 anodic. It will be obvious that if the barrier 3 is instead anion selective, the potential of the electrodes must be reversed.

If dissociation of the ligate(s) is effected by an electrically controlled change in ionic strength as described above and if the barrier 3 is ion selective then it may be advantageous if the barrier 4 has the opposite ion-selectivity, i.e. if barrier 3 is cation-selective, then barrier 4 may be advantageously anion-selective.

Ligates may also be dissociated from the biospecific surface by establishing a substantial voltage gradient (e.g. in the range of from about 10 to about 100 volts per centimeter) at the biospecific surface. The polarity of the applied voltage should be such as to pull the ligate(s) from the surface into the bulk liquid in compartment 6 and therefore will be determined in part by the isoelectric point of the ligate and the pH of liquid in compartment 6. The desorbed ligate(s) must migrate only a short distance (of the order of 0.1 mm) to arrive at a position in compartment 6 from which it (they) can be swept out by a flow in the compartment. Hence the high voltage gradient will have to be applied generally for a period of only some minutes. Depending upon the composition of the liquids in compartments 6, 7, and 8, the heat generated by the applied voltage gradient may nevertheless be excessive in which case the contents of compartments 7 and 8 may be advantageously recirculated through an external heat exchanger, absorbing heat from compartment 6 through barriers 3 and 4.

Although the process and apparatus of this invention have been described for the sake of simplicity in terms of barriers and electrodes which are planar, flat sheets, it will be understood that other configurations may be advantageously used. For example, referring again to FIG. 1(b), the electrodes and barriers may be arranged as concentric cylinders, in which case the central electrode may have the form of a rod or wire. If it is desired to have several biospecific surfaces between a single pair of electrodes then, for example, barriers 3 and 4 with suitable structure (such as an open screen or nets) between them may be wound as a spiral around a central cylindrical, rod or wire electrode and enclosed by a cylindrical outer electrode.

A second embodiment of this invention may be described with reference to FIG. 1(c) in which both barriers 3 and 4 have biospecific surfaces arranged to contact the contents of compartment 6. Three modes of desorption of ligate 9 may be described. In the first, the dissociating agent is first transferred from compartment 7 to the biospecific surface on barrier 3 and after an appropriate interval (with or without passage of a maintenance current) the contents of compartment 6 are swept out. The polarity of the electric current is subsequently reversed and the dissociating agent (generally the same one used in the prior step) is transferred electrically from compartment 8 to the biospecific surface on barrier 4 and after an appropriate interval the contents of compartment 6 are again swept out.

Alternatively the transfer of the dissociating agent may be continued through one barrier only until the pH, ionic strength or concentration of chaotropic agent is sufficient at both biospecific surfaces to result in dissociation of the ligate(s) from the ligand(s). After an appropriate interval the contents of compartment 6 are flushed out.

In a third embodiment, one of barriers 3 and 4 is ion selective and the other has alternatively no ion selectivity, substantially less selectivity of the same sign or has selectivity of the opposite sign. In such case the direction of the applied electric current is such as to increase the ionic strength in compartment 6 if the ligate will be dissociated by such an increase. As is well known in the art, if the barriers are ion selective, then a substantial concentration gradient will be established at the biospecific surfaces, higher at the surfaces than in the builk liquid, thereby facilitating desorption.

On the other hand if the ligate will be dissociated by a decrease in ionic strength, then the direction of the electric current should be such as to decrease the ionic strength in compartment 6. Again, as is well known in the art, if the barriers are ion selective then a substantial concentration gradient will be established at the biospecific surfaces, lower at the surfaces than in the bulk liquid, again thereby facilitating desorption.

Figure 2:
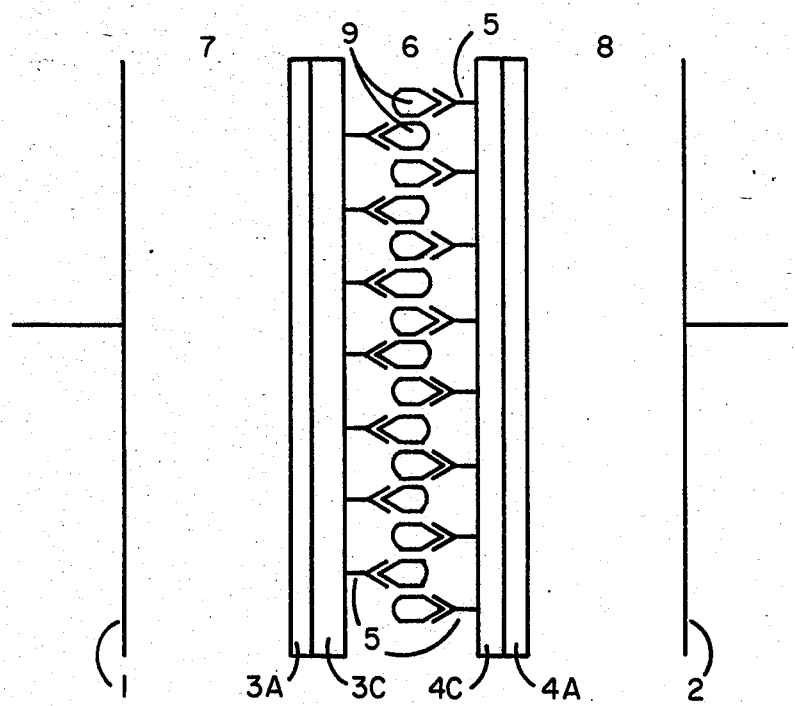
FIG. 2 is a schematic representation of a third embodiment of an apparatus having electrolytically conducting biospecific absorbing barriers in accordance with the present invention, in the sorbed state.

A fourth embodiment of the invention maybe described with respect to FIG. 2 in which either or both of the barriers 3 and 4 are bipolar ion selection membranes. For example regions 3a and 4a may comprise anion selective material and regions 3c and 4c cation selective material. When electrode 1 is made anodic and electrode 2 cathodic, the interface between regions 3a and 3c, rapidly becomes substantially depleted of electrolyte. If passage of electric current is thereafter continued it will be carried through region 3a by hydroxide ions resulting from the dissociation of water at or near the interface between regions 3a and 3c. Current through region 3c will be carried by hydrogen ions (resulting from such water dissociation) into the biospecific surface of barrier 3 resulting in dissociation of ligate-ligand complexes. After an appropriate interval, the contents of compartment 6 will be swept out together with the dissociated ligate. The direction of the electric current may then be reversed causing hydrogen ions generated at the interface between regions 4a and 4c to dissociate ligand-ligate complexes at the biospecific surface of barrier 4. After an appropriate interval the contents of compartment 6 are again swept out.

It can be appreciated that if a single pass of the liquid through one electrical stage electrolytic cell unit does not adsorb or desorb the required amount of the component of interest, a series of units can be arranged in which the liquid flows in series through each electrical stage, with each adsorbing or desorbing in one pass an aliquot share of the said component. Each electrical stage may in time contain one or more hydraulic stages between electrodes as is well known in the electrolytic cell art. Alternatively, a single stage unit can be employed by which the liquid is continuously recirculated therein in a batch mode until the required adsorbtion or desorbtion is attained. The number of compartments in each electrical stage and the number of stages in series flow can of course be varied depending upon the particular application and production rate required.

The following non-limiting examples illustrate the present invention;

EXAMPLE 1

Figure 1B:
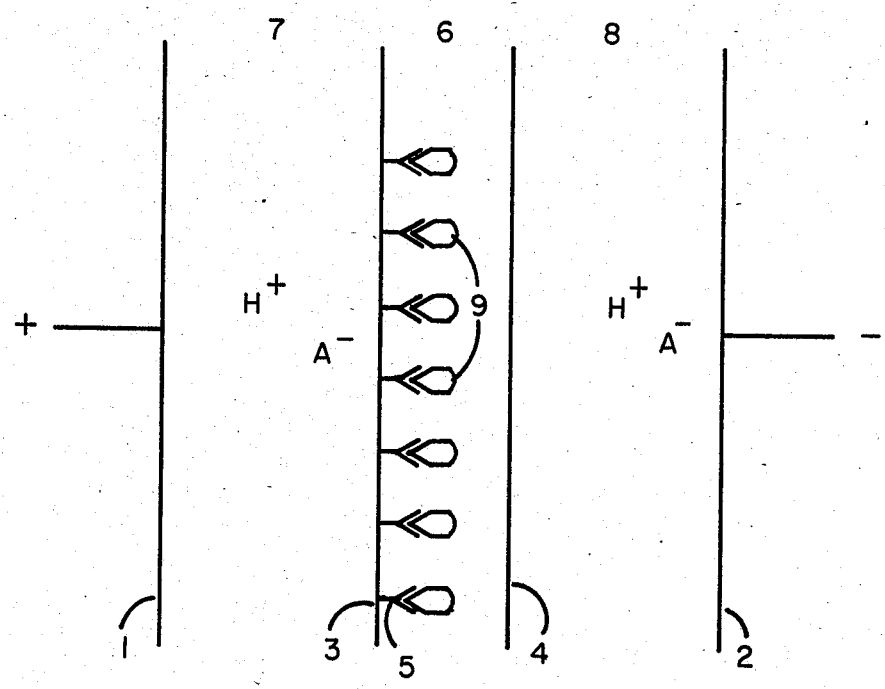
Figure 1C:
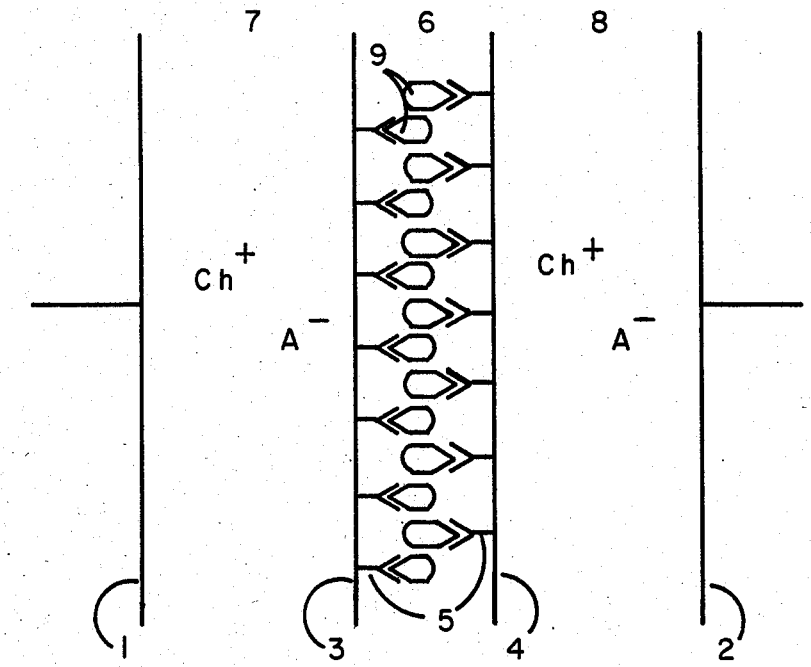

A 3-compartment apparatus is constructed in accordance with FIG. 1(c). The barriers comprise agarose/acrylamide copolymer hydrous gels reinforced with a fabric woven from spun, modacrylic staple. The barriers have dimensions of about 15.2 by 7.6 cm. and are about 0.06 cm thick. The electrodes are platinized titanium of the same dimensions. The electrodes and barriers are separated by linear low-density polyethylene tortuous path spacers about 0.05 cm thick available from Ionics, Inc. of Watertown, Mass. and having an effective area of about 15 cm$^2$. The flow path contains convection promoters. One face of each barrier contains a high density of L-lysine groups coupled to the barrier by cyanogen bromide. The apparatus is assembled with the biospecific surfaces of the barriers facing the central compartment (corresponding to compartment 6 in FIG. 1(c)). The central compartment is rinsed with about 0.1 molar sodium hydrogen phosphate buffer having a pH of about 7.4. Ten ml of human blood plasma are diluted 1:1 with distilled water and recirculated through the central compartment several times. The compartment is drained and then rinsed for several minutes with about 0.3 molar sodium hydrogen phosphate buffer having a pH of about 7.4. The compartment is left filled with the buffer. A 0.3 molar solution of epsilon-aminocaproic acid adjusted to a pH of about 11 with sodium hydroxide is circulated through the cathode compartment and 0.3M epsilon-aminocaproic acid solution adjusted to a pH of about 4.5 with hydrochloric acid is circulated through the anode compartment. A current of about one ampere is passed for a few minutes. The contents of the center compartment 6 are flushed out immediately or after waiting a few minutes and are found to contain about 50 micrograms of plasminogen.

EXAMPLE 2

A 3-compartment apparatus is constructed in accordance with FIGS. 1(a) and 1(b). Barrier 3 is prepared from cellulose acetate membrane filter sheets having dimensions of about 15.2 by 7.5 cm. The sheet is first soaked in succession in 0.1 molar HCl, in distilled water and in 0.1 molar NaOH. It is then washed in distilled water and then successively with 20%, 40%, 60%, 80% and 100% by volume of dioxane in water. The sheet is thereafter reacted for about 30 minutes at about 50° C. in approximately 0.5 molar solution of diisopropylethylamine in dioxane. A solution of trichloro-s-triazine in dioxane is added and the reaction continued for about 1 hour. The sheet is rinsed in dioxane and then reacted for about 30 minutes in a 2 molar solution of aniline in dioxane. Thereafter the sheet is rinsed successively in 80%, 60%, 40%, 20% and 0% by volume of dioxane in water. The resulting wet sheet is mounted as barrer 3 in the cell of FIGS. 1(a) and 1 (b). The electrodes and spacers are similar to those used in Example 1. Barrier 4 is a CR61 CZL cation selective membrane avilable from Ionics, Inc., Watertown, MA. A solution of monoclonal anti-Hepatitis-B-Surface-antigen-IgM having about 1 milligram of antibody per milliliter of solution is circulated through the central compartment at about 4° C. for about 24 hours. The solution is about 0.1 molar in sodium hydrogen phosphate, about 0.1 molar in sodium chloride and has a pH of about 8.6. The solution is subsequently drained and the compartment rinsed with the phosphate/chloride buffer solution. Hepatitis B surface antigen positive serum diluted with phosphate buffered saline containing 1% bovine serum albumin and having about 40 micrograms of antigen per milliliter is recirculated through the central compartment. The antigen solution is drained and the compartment rinsed with phosphate/chloride buffer and then filled with fresh buffer solution. A 0.05 molar glycine HCl solution (pH 2.2) is circulated through compartment 7 (the anode compartment in this case) and phosphate/saline buffer through the cathode compartment (compartment 8 in this case). A current of about one ampere is passed for several minutes and the contents of the central compartment are then flushed out with phosphate/chloride buffer. The recovered antigen is found to be immune reactive.

EXAMPLE 3

A 3-compartment apparatus is constructed in accordance with FIGS. 1(a) and 1(c). Barrier 3 is prepared from Cuprophane ® dialysis membrane having dimensions of about 15.2 by 7.6 cm. The sheet is activiated with tosyl chloride and then mounted in the apparatus of Example 2 as Barrier 3. Barrier 4 is a CR61 CZL cation selective membrane as in Example 2. The central compartment is rinsed with phosphate/chloride buffer and then a solution of anti-Factor VIII c in phosphate/chloride buffer is recirculated through the central compartment for about 24 hours at about 4° C. The compartment is drained and rinsed with buffer solution. Cryoprecipitate from human blood plasma is dissolved in phosphate/chloride buffer to give a solution having about 20 milligrams of protein per milliliter. This solution is recirculated through the central compartment. The partially depleted cryoprecipitate solution is drained from the compartment which is then rinsed with fresh buffer. An approximately 3 molar solution of sodium thiocyanate of about pH 7 is recirculated through compartments 7 and 8. Electrode 1 is made cathodic and electrode 2 anodic. A current of about 1 ampere is passed for several minutes. Thereafter the contents of the central compartment are rapidly flushed out with buffer solution and immediately dialyzed to reduce the concentration of chaotropic agent as rapidly as possible. The recovered desorbate is found to contain undenatured FVIII.

EXAMPLE 4

A 3-compartment apparatus is constructed in accordance with FIGS. 1(a) and 1(b). Barrier 3 is an anion-selective membrane having a macroreticular surface prepared in accordance with the teachings of U.S. Pat. Nos. 3,749,655 and 3,926,864 from divinyl benzene and vinyl benzyl chloride. The macroreticular surface is treated with an aqueous solution of N,N dimethyl ethanolamine and subsequently the entire membrane is treated with an aqueous solution of trimethyl amine. The macroreticular surface is next treated with bisepoxirane and subsequently with normal octyl alcohol to introduce hydrophobic octyl groups into the macroreticular surface. A piece of said membrane approximately 15.2 by 7.6 cm and having a thickness of about 0.06 cm is mounted in the apparatus of Example 2 as Barrier 3 with the macroreticular surface facing the central compartment. Barrier 4 is a CR61 CZL cation selective membrane as in Example 2. The central compartment is rinsed with 1 molar ammonium sulfate. A solution having about 1 milligram of catalase (asperigillus niger) per milliliter of molar ammonium sulfate is circulated through the central compartment which is subsequently drained and rinsed with molar ammonium sulfate. The compartment is filled with a solution one molar in ammonium sulfate and 4 molar in urea. A solution of 0.1 molar ammonium sulfate is circulated through compartments 7 and 8. Electrode 1 is made anodic and electrode 2 cathodic. A potential of about 10 volts is maintained across the electrodes. The initial current decreases rapidly and when after several minutes it reaches a steady state value, the contents of the central compartment are flushed out, and dialyzed rapidly to reduce the concentration of urea. It is found that the desorbate contains active catalase.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent assemblies and methods.

What is claimed is:

1. A method of recovering biospecifically, sorbable components dispersed in an aqueous solution comprising:
   (a) contacting said solution as a first solution with an electrolytically conducting barrier having biospecific sorbing properties for at least one of said components whereby a substantial fraction of said components in said solution having biospecific binding affinity for said barrier is sorbed by said barrier;
   (b) removing said first solution from contact with the said barrier;
   (c) contacting said barrier with a second aqueous solution;
   (d) passing a direct electric current through said barrier and said second solution in a direction approximately parallel to the smallest dimension of said barrier thereby facilitating the desorption of at least one of said components having biospecific binding affinity for the said barrier into said second solution; and
   (e) removing said second solution from contact with said barrier.

2. Apparatus for recovering biospecifically, sorbable components dispersed in an aqueous solution comprising:
   (a) an electrolytically conducting barrier having biospecific sorbing properties for at least one of said components;
   (b) means for contacting said solution with said barrier whereby components in said solution having biospecific binding affinity for said barrier are at least in part sorbed by said barrier;
   (c) means for removing said solution from contact with said barrier;
   (d) means for contacting said barrier with a second aqueous solution as a receiving solution;
   (e) means for passing a direct electric current through said barrier and said second solution in a direction approximately parallel to the smallest dimension of said barrier thereby to facilitate the desorption from said barrier of at least one of said components having biospecific binding affinity for said barrier into said second solution and (f) means for removing said second solution from contact with said barrier.

3. Apparatus according to claim 2 in which said barrier has the form of a cylinder.

4. Apparatus according to claim 2 in which said barrier has the form of a spiral.

5. Apparatus according to claim 2 in which said barrier contain ligands selected from the group consisting of enzyme inhibitors, enzyme substrate analogues, coenzymes, apoenzyme polymeric substrates, enzymes, nucleic acid complementary strands, haptens, antibodies, monosaccharides, polysaccharides, lectins, small target compounds for binding proteins, binding proteins, aminobenzamidine, 5' adenosine monophosphate, S. aureus Protein A, hormones, hormone receptors, and immobilized textile dyes.

6. Apparatus according to claim 2 in which said barrier is selected from the group consisting of ion-selective membranes, sheets of hydrous gels and porous sheets having average pore sizes of less than about 10 micrometers.

7. Apparatus according to claim 2 in which said barrier is a macroreticular ion-selective membrane.

8. Apparatus according to claim 2 in which said barrier is an ion-selective membrane having ligands attached to a macroreticular surface.

9. Apparatus according to claim 2 in which said barrier is a bipolar ion selective membrane.

* * * * *